United States Patent
Dutta et al.

(10) Patent No.: US 11,028,249 B2
(45) Date of Patent: Jun. 8, 2021

(54) METHODS OF SYNTHESIZING IONIC LIQUIDS FROM PRIMARY ALCOHOL-CONTAINING LIGNIN COMPOUNDS

(71) Applicant: National Technology & Engineering Solutions of Sandia, LLC, Albuquerque, NM (US)

(72) Inventors: Tanmoy Dutta, Berkeley, CA (US); Blake Simmons, San Francisco, CA (US); Seema Singh, Mountain House, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/119,866

(22) Filed: Aug. 31, 2018

(65) Prior Publication Data

US 2019/0062519 A1 Feb. 28, 2019

Related U.S. Application Data (60) Provisional application No. 62/553,060, filed on Aug. 31, 2017.

(51) Int. Cl.
| | |
|---|---|
| *C08J 11/28* | (2006.01) |
| *C08L 97/02* | (2006.01) |
| *C08J 11/16* | (2006.01) |
| *C08L 97/00* | (2006.01) |
| *C07C 209/00* | (2006.01) |

(Continued)

(52) U.S. Cl.
CPC ............ *C08J 11/28* (2013.01); *C07C 41/22* (2013.01); *C07C 209/00* (2013.01); *C07C 209/08* (2013.01); *C08H 6/00* (2013.01); *C08J 11/16* (2013.01); *C08L 97/005* (2013.01); *C08L 97/02* (2013.01); *C08J 11/10* (2013.01); *C08J 2397/02* (2013.01)

(58) Field of Classification Search
None
See application file for complete search history.

(56) References Cited

U.S. PATENT DOCUMENTS 3,595,915 A * 7/1971 Emerson ............... C07C 323/00
564/209
5,959,167 A * 9/1999 Shabtai .................. C10G 1/002
585/240

(Continued)

FOREIGN PATENT DOCUMENTS

DE 102006011077 A1 9/2007
WO 2014/172042 A1 10/2014

OTHER PUBLICATIONS

Adbel-Magid et al., "Reductive Amination of Aldehydes and Ketones with Sodium Triacetoxyborohydride. Studies on Direct and Indirect Reductive Amination Procedures1", *J. Org. Chem*, 61(11):3849-3862 (1996).

(Continued)

*Primary Examiner* — Peter A Salamon
(74) *Attorney, Agent, or Firm* — Kilpatrick Townsend & Stockton LLP (57) ABSTRACT

Methods and compositions are provided for synthesizing ionic liquids from lignin. Methods and compositions are also provided for treating lignin with ionic liquids.

20 Claims, 1 Drawing Sheet

X⁻ = acetate anion (51) Int. Cl.
*C07C 41/22* (2006.01)
*C07C 209/08* (2006.01)
*C08H 7/00* (2011.01)
*C08J 11/10* (2006.01)

(56) References Cited

U.S. PATENT DOCUMENTS

| | | | | |
|---|---|---|---|---|
| 6,824,599 B2* | 11/2004 | Swatloski | ............... | C08B 1/003 |
| | | | | 106/163.01 |
| 2008/0185112 A1* | 8/2008 | Argyropoulos | ........ | C07H 19/01 |
| | | | | 162/9 |
| 2009/0203898 A1* | 8/2009 | Buchanan | ............... | C08B 1/003 |
| | | | | 536/58 |
| 2012/0011886 A1* | 1/2012 | Shiflett | .................. | C09K 5/047 |
| | | | | 62/476 |
| 2014/0243511 A1* | 8/2014 | Tamminen | ............... | C07G 1/00 |
| | | | | 530/500 |
| 2015/0122246 A1* | 5/2015 | Sun | .......... | C13K 1/02 |
| | | | | 127/37 |
| 2016/0031843 A1* | 2/2016 | Socha | ................... | C07C 209/28 |
| | | | | 514/471 |
| 2016/0122379 A1* | 5/2016 | Singh | ....... | D21C 3/20 |
| | | | | 530/507 |
| 2019/0062519 A1* | 2/2019 | Dutta | ...................... | C07C 41/22 |

OTHER PUBLICATIONS

Alhede, et al., "Preparation of 5-[[(2-aminoethyl)thio]methyl]-2-furanmethanol derivative," CAS 110:94977, 1989.

Dizhbite, et al., "Products of lignin modification: promising adsorbents of toxic substances," CAS 139: 86842, 2003.

Foo, et al., "Absorption cycle utilizing ionic compounds and/or non-ionic absorbents as working fluids," CAS 167:382562, 2016.

Liang, et al., "Synthesis and characterization of quaternary ammonium-based ionic liquids," CAS 157: 437855, 2012.

Pratap, et al., "Preparation of (R)-(−)- / (S)-(+) -7- [3-n-substituted amino-2-hydroxypropoxy] flavones as antidyslipidemic agents," CAS 148: 238941, 2008.

Shiflett, et al., "Ionic compounds in lithium bromide/water absorption cycle systems," CAS 167: 382565, 2016.

Socha, et al., "Efficient biomass pretreatment using ionic liquids derived from lignin and hemicellulose," PNAS, published online Aug. 18, 2014, E3587-E3595.

Srinivasan, et al, "Process for preparation of ezetimibe," CAS 152: 97325, 2009.

* cited by examiner

FIG. 1

⊖X = acetate anion

FIG. 2

● = oligomeric lignin

⊖X = acid anion

METHODS OF SYNTHESIZING IONIC LIQUIDS FROM PRIMARY ALCOHOL-CONTAINING LIGNIN COMPOUNDS

CROSS-REFERENCES TO RELATED APPLICATIONS

The present application claims priority to U.S. Provisional Pat. Appl. No. 62/553,060, filed on Aug. 31, 2017, which application is incorporated herein by reference in its entirety.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in the invention.

BACKGROUND OF THE INVENTION

Lignocellulosic biomass, which is comprised of lignin, cellulose and hemicellulose, typically constitutes about 85% mass of most plant biomass. Derived from agricultural wastes, forest residues and dedicated energy crops, lignocellulosic biomass is used by biorefiners and pulp and paper manufactures to extract and produce valuable materials. The processing of lignocellulosic biomass will, in turn, also produce lignin, cellulose and hemicellulose as the main byproducts. Often, the lignin from biorefineries and pulp and paper manufacturers is combusted to generate heat, steam, or electricity. However, this use of lignin provides minimal economic value as compared to other sources of heat, steam, or electricity such as natural gas. Further, new and more energy efficient plants can produce more lignin than they require for generation of heat, steam, and electricity. Unfortunately there is no proper application of lignin byproducts apart from generation of heat. Thus, new technologies are needed to convert polymeric lignin produced by biorefiners and pulp or paper manufacturers into higher value products.

In recent years, tremendous effort has been applied to develop methods for production of useful compounds from lignocellulosic biomass, such as ionic liquids. Ionic liquids (ILs) are used as powerful solvents (in chemical reactions, biomass pretreatment, and the like), electrolytes, heat transfer liquids, and various other important applications. Development of a simple and economic route to synthesize ionic liquids from the lignin, hemicellulose, and their depolymerized products will not only reduce ionic liquid production cost, but also will demonstrate a route to synthesize ionic liquids from renewable resources.

What is desired is a process which can convert lignin, hemicellulose and their depolymerized products (both monomeric and oligomeric) to ILs in simple, inexpensive and fewer synthetic steps. It is also desirable to change the structure of the cation and the anions to tailor-made-ILs suitable for various applications, such as solvents for chemical reactions, biomass pretreatment, batteries, electrolytes, and the like. Methods for the synthesis of tertiary and quaternary ammonium salt-based ILs from aromatic aldehydes, derived from lignin and hemicellulose, have recently been developed. See, Socha, A. M. et al., *Proceedings of the National Academy of Sciences,* 2014, 111(35): E3587-E3595. Synthetic routes that transform aromatic aldehydes to ammonium salt-based ILs via imine formation and reductive amination require reagents such as sodium triacetoxyborohydride reagent (~$127/100 g). The present invention introduces an alternative route to ammonium salt-based ILs, starting with aromatic primary alcohols and less expensive reagents, such as thionyl chloride (~$8/100 g). Other advantages of the invention will be made clear throughout the description below.

BRIEF SUMMARY OF THE INVENTION

In some embodiments, the present invention provides a process for preparing an ionic liquid comprising: contacting a lignin-derived aromatic starting material with a halogenating agent under conditions sufficient to form a lignin-derived aromatic halide; contacting the lignin-derived aromatic halide with an amine under conditions sufficient to form a lignin-derived aromatic amine; and contacting the lignin-derived aromatic amine with an acid under conditions sufficient to form a lignin-derived aromatic ammonium salt, thereby preparing the ionic liquid.

In some embodiments, the lignin-derived aromatic starting material comprises a primary alcohol. In some embodiments, the lignin-derived aromatic starting material comprises one or more components selected from the group consisting of depolymerized lignin monomers, oligomeric lignin, polymeric lignin, and lignocellulose. In some embodiments, depolymerized lignin monomers comprise one or more components selected from the group consisting of modified phenols, modified anisoles, modified guaiacols, modified veratroles, modified catechols, and modified syringols.

In some embodiments, the halogenating agent is selected from the group consisting of hydrogen chloride, thionyl chloride, phosphorus trichloride, phosphorus pentachloride, hydrogen bromide, thionyl bromide, phosphorus tribromide, phosphorus pentabromide, and phosphorus triiodide. In some embodiments, the lignin-derived aromatic halide is a chloride, a bromide, or an iodide.

In some embodiments, the amine is a secondary amine or a tertiary amine.

In some embodiments, the acid is selected from the group consisting of acetic, sulfuric, and phosphoric acid.

Further aspects and embodiments of the invention are described in detail below.

DETAILED DESCRIPTION OF THE INVENTION

I. Introduction

Lignin, the second most abundant biopolymer on Earth, is a heterogeneous macromolecule largely comprised of the three phenylpropane units (also referred to as monolignols): p-coumaryl alcohol, coniferyl alcohol, and sinapyl alcohol. The monolignol composition of lignin varies as a function of its origin (hardwood, softwood or grass) and the method used for its extraction from biomass. The present invention provides a method for easy conversion of lignin starting material (i.e., depolymerized lignin monomers, oligomeric lignin, polymeric lignin, and lignocellulose) into ionic liquids (ILs).

The method utilizes the functional groups of the aromatic lignin molecules. These functional groups (i.e., alcohols, aldehydes, and carboxylic acids) can serve as chemical "handles" upon which to convert lignin-derived monomers, oligomers, and polymers into ionic liquids. In particular, the method is capable of transforming the primary alcohols of the lignin-derived aromatic moieties to tertiary or quaternary ammonium salt-based ILs via halogenation, amination and protonation reactions.

Advantageously, the method employs inexpensive materials and convenient reaction conditions. The IL synthesis is a direct route which requires minimal purification or no purification. The synthetic steps can easily be conducted as a one pot process, which can be readily applied to a complex mixture of depolymerized lignin monomers, oligomeric lignin, polymeric lignin, and/or lignocellulose. Thus, the method of the present invention produces ionic liquids at a reduced cost.

II. Definitions

"Ionic liquid" refers to salts that are liquids at or near room temperature, rather than solids, such as crystals. Ionic liquids typically exhibit a number of advantageous properties, including low volatility, thermal stability, and the ability to dissolve a wide range of solutes under mild conditions.

"Contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

"Lignin" and "polymeric lignin" refer to a phenylpropane polymer of monolignol monomers. Polymeric lignin is an integral part of the lignocellulosic biomass, generally present in the secondary cell walls of plants and certain types of algae. In general, polymeric lignin contains one or more crosslinked guaiacyl groups, and/or one or more crosslinked syringyl groups, and/or one or more crosslinked p-hydroxyphenyl groups. Polymeric lignin will range in molecular weight (i.e., weight average molecule weight "$M_w$") from about 1,000 g mol$^{-1}$ to 100,000 g mol$^{-1}$. One of skill in the art will appreciate that the average molecular weight of a particular polymeric lignin depends on factors such as the source of the polymeric lignin and the method used for isolating the material from the source.

"Lignin monomers," "monomeric lignin," "monolignol," "monolignol monomers," and "lignol" refer to the group of monomeric aromatic compounds consisting of p-coumaryl alcohol, coniferyl alcohol, sinapyl alcohol, their modified derivatives, and mixtures thereof. As used herein, the term "depolymerized lignin monomers" refers to a composition comprising a mixture of monomeric lignin produced by breaking down lignin using any method known to those skilled in the art. Examples of depolymerized lignin monomers include, but are not limited to phenols, anisoles, guaiacols, veratroles, catechols, and syringols.

"Lignin oligomers" and "oligomeric lignin" refer to lignin compounds that contain from 2 to about 10 lignin monomers. In general, oligomeric lignin contains one or more crosslinked guaiacyl groups, and/or one or more crosslinked syringyl groups, and/or one or more crosslinked p-hydroxyphenyl groups. Oligomeric lignin ranges in molecular weight ($M_w$) from about 200 g mol$^{-1}$ to 1,000 g mol$^{-1}$. One of skill in the art will appreciate that the average molecular weight of a particular oligomeric lignin depends on factors such as the source of the oligomeric lignin and the method used for isolating the material from the source.

"Lignocellulosic biomass" and "lignocellulose" refer to natural and/or synthetic materials containing lignin, cellulose, and/or hemicellulose. Generally, these materials also contain (but need not contain) xylan, protein, and/or other carbohydrates, such as starch.

As used herein, the term "cellulose" refers to refers to a homopolymer of β(1→4) linked D-glucose units that form a linear chain. Cellulose can contain several hundred to several thousand or more glucose units, making cellulose a polysaccharide.

As used herein, the term "hemicellulose" refers to a heteropolymer containing different saccharide units, including but not limited to, xylose, mannose, galactose, rhamnose and arabinose. Hemicellulose forms a branched polymer with several hundred to several thousand sugar units. Hemicellulose can include both pentose and hexose sugars.

The term "lignin-derived," as it is used herein to refer to a starting material, ionic liquid, or other material, means that the material can be obtained by converting lignocellulosic biomass to said material. Conversion of lignin or lignocellulosic biomass to a lignin-derived material can be accomplished by chemical, biochemical, and/or physical means as described herein.

"Lignin-derived aromatic starting material" refers to a mixture containing one or more aromatic functional groups that are obtained from lignin, lignocellulose, or lignocellulosic biomass.

"Aromatic" and "aryl" refer to a group of ring structures having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. Aromatics include any group that is inclusive of both aryl and heteroaryl groups. Aromatics include, but are not limited to, benzene, phenol, toluene (methyl benzene), ethyl benzene, propyl benzene, xylenes (ortho-, meta-, and para-dimethyl benzene compounds), and various dialkyl substituted benzene compounds, such as the isomeric methylethyl benzene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein.

"Aldehyde" refers to an organic compound containing the structure R—CHO, consists of a carbonyl center (a carbon double bonded to oxygen) bonded to hydrogen and an R group, which is any generic side chain.

"Alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec_butyl, tert_butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Hydroxyl" or "hydroxy" as used herein are represented by the formula —OH.

"Halogenating agent" refers to a group of compounds capable of converting alcohols to halides. "Halide" refers to a fluoride, chloride, bromide, iodide, or astatide ion or compound. Halogenating agents useful in the present invention include hydrogen chloride, hydrogen bromide, hydrogen iodide, thionyl chloride, thionyl bromide, phosphorus trichloride, phosphorus tribromide, phosphorus triiodide, phosphorus pentachloride, phosphorus pentabromide, or oxalyl chloride, and the like.

"Alcohol" refers to an alkyl group, as defined herein, having a hydroxy group attached to a carbon of the chain. Alcohols useful in the present invention include primary alcohols. "Primary alcohol" refers to an alcohol having the hydroxy group connected to a primary $sp^3$-hybridized carbon atom of an alkyl group, represented by the formula —$CH_2OH$. One of skill in the art will appreciate that other alcohols are useful in the present invention.

"Lignin-derived aromatic halide" refers to any aromatic halide containing compounds that are synthesized from a lignin-derived aromatic starting material and a halogenating agent as described herein.

"Amine" refers to an $NR_3$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen). Tertiary amines can be protonated to form cations. A "tertiary ammonium" is a protonated tertiary amine of the general formula $HNR_3^+$, where R is not H. A "quaternary ammonium" is an ammonium cation of the general formula $NR_4^+$, where R is not H.

"Alkyl amine" and "alkylamine" refer to an alkyl group as defined herein, having one or more amino groups. The amino groups can be primary, secondary or tertiary. The alkyl amine can be further substituted with a hydroxy group to form an amino-hydroxy group. The alkyl amine can be a monoalkylamine, dialkylamine, or trialkylamine. Alkyl amines useful in the present invention include, but are not limited to, methyl amine ethyl amine, propyl amine, isopropyl amine, butyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Lignin-derived aromatic amine" refers to any aromatic amine containing compounds that are synthesized from a lignin-derived aromatic halide and an amine as described herein.

"Acid" refers to compounds that are capable of donating a proton ($H^+$) under the Brønsted-Lowry definition, or are electron pair acceptors under the Lewis definition. Acids useful in the present invention include Brønsted acids that include, but are not limited to, acetic acid, tartaric acid, formic acid, lactic acid, citric acid, sulfuric acid, hydrochloric acid, nitric acid, boric acid, phosphoric acid, hydrofluoric acid, hydrobromic acid, and perchloric acid. Amino acids are also useful in the present invention and include, but are not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Other organic acids and mineral acids are useful in the present invention.

"Lignin-derived aromatic ammonium salt" refers to any aromatic ammonium salt containing compounds that are synthesized from a lignin-derived aromatic amine and an acid as described herein. The lignin-derived aromatic ammonium salt contains an ammonium cation (e.g., tertiary ammonium cation or quaternary ammonium cation) and a counter anions (e.g., halide, dihydrogenphosphate, dihydrogensulfate, formate, acetate, lysinate, etc.). One of skill in the art will appreciate that other counter anions are useful in the present invention.

"Polar solvent" as used herein refers to solvents with a dielectric constant of about 6 or greater. Polar solvents include protic and aprotic solvents. "Protic solvents" refer to solvents that solubilize anions via hydrogen bonding and include n-butanol, isopropanol, n-propanol, ethanol, methanol, nitromethane, and water. "Aprotic solvents" solvate cations via interaction with their negative dipole and include dichloromethane, tetrahydrofuran, ethyl acetate, acetone, dimethylformamide, acetonitrile, dimethyl sulfoxide, and propylene carbonate.

"Non-polar solvent" as used herein refers to solvents with a dielectric constant of less than about 6. Non-polar solvents interact with other compounds or themselves predominantly through dispersion forces. Non-limiting examples of non-polar solvents include toluene, benzene, xylene, n-heptane, octane, isooctane, cyclohexane, hexane, pentane, chloroform, diethyl ether and 1,4-dioxane.

The terms "about" and "around," as used herein to modify a numerical value, indicate a close range surrounding that explicit value. If "X" were the value, "about X" or "around X" would indicate a value from 0.9X to 1.1X, or a value from 0.95X to 1.05X, or a value from 0.98X to 1.02X, or a value from 0.99X to 1.01X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.99X."

III. Methods for Preparing Ionic Liquids

In one aspect, the invention provides a method for preparing an ionic liquid. The method includes:
contacting a lignin-derived aromatic starting material with a halogenating agent under conditions sufficient to form a lignin-derived aromatic halide;
contacting the lignin-derived aromatic halide with an amine under conditions sufficient to form a lignin-derived aromatic amine; and
contacting the lignin-derived aromatic amine with an acid under conditions sufficient to form a lignin-derived aromatic ammonium salt, thereby preparing the ionic liquid.

Lignin is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin that consists almost entirely of G with small quantities of H. That of dicotyledonous angiosperms is more often than not a mixture of G and S (with very little H), and monocotyledonous lignin is a mixture of all three. Many grasses have mostly G, while some palms have mainly S. Lignin generally contain small amounts of incomplete or modified monolignols, and other monomers are prominent in non-woody plants. Unlike cellulose and hemicellulose, lignin cannot be depolymerized by hydrolysis. Cleavage of the principal bonds in the lignin polymer generally proceeds through oxidation.

In some embodiments, the lignin is provided as lignocellulosic biomass. As used herein, the phrase "biomass" refers to lignocellulosic materials comprised of lignin-containing any mix of cellulose, hemicelluloses, and lignin as the major constituents. In the context of this invention "lignocellulosic biomass" and "lignocellulose" are used interchangeably with "cellulosic biomass," and refer to biomass that comprises lignin. "Biomass" for use in the process of the present invention includes any biomass or mixtures thereof that contains lignin or lignocellulose. Lignocellulose-containing biomass primarily consists of cellulose, hemicelluloses, and lignin. Woody biomass, for instance, is about 45-50% cellulose, 20-25% hemicellulose and 20-25% lignin. Herbaceous materials have lower cellulose, lower lignin and higher hemicellulose contents.

Cellulose is a linear β1-4 linked polymer of glucose. It is the principal component of all higher plant cell walls. In nature, cellulose exists in crystalline and amorphous states. The thermodynamic stability of the β1-4 linkage and the capacity of cellulose to form internal hydrogen bonds gives it great structural strength. Cellulose is degraded to glucose through hydrolytic cleavage of the glycosidic bond. Hemicellulose is a term used to refer to a wide variety of heteropolysaccharides found in association with cellulose and lignin in both woody and herbaceous plant species. The sugar composition varies with the plant species, but in angiosperms, the principal hemicellulosic sugar is xylose. Like cellulose, xylose occurs in the β1-4 linked backbone of the polymer. In gymnosperms, the principal component sugar is mannose. Arabinose is found as a side branch in some hemicelluloses.

In a some embodiments, the lignocellulosic biomass includes, but is not limited to, switchgrass, pine, eucalyptus, corn stover, corn fiber, hardwood, such as poplar and birch, softwood, cereal straw, such as, wheat straw, switch grass, Miscanthus, rice hulls, or mixtures thereof. Other examples include corn fiber, rice straw, wheat bran, pine wood, wood chips, poplar, bagasse, paper and pulp processing waste.

In some embodiments, the lignin is obtained via chemical or enzymatic hydrolysis of lignocellulosic biomass. For example, lignocellulosic biomass can be treated with hot water, carbon dioxide, acid, or base, or a combination thereof in order to obtain lignin from the biomass. Ionic liquids (including, but not limited to, 1-ethyl-3-methylimidazolium acetate) can be used in treatment methods to dissolve biomass and recover lignin and cellulose for further processing as described, for example, in U.S. Pat. Appl. Pub. No. 2012/0301948 and Intl. Pat. Appl. Pub. No. WO 2016/070125, which are incorporated herein by reference. Biomass can also be subjected to the action of one or more proteases, lipases, cellulases, amylases, glucanohydrolases, pectinases, xylanases, ferulic acid esterases, mannanases, or hemicellulases. The pretreated biomass may also be treated with other enzymes, e.g., hemicellulases, that are used for the degradation of biomass.

A "cellulase" as used herein is a glycoside hydrolase enzyme that hydrolyzes cellulose (β-1,4-glucan or β-D-glucosidic linkages) resulting in the formation of glucose, cellobiose, cellooligosaccharides, and the like. In the context of the present invention, cellulases include endoglucanases; exoglucanases or cellobiohydrolases; and β-glucosidases. Endoglucanases (EC 3.2.1.4) including endo-1,4-β-glucanases or 1,4β-D-glucan-4-glucanohydrolases, act randomly on soluble and insoluble 1,4-β-glucan substrates. Exoglucanases (exo-1,4-β-D-glucanases, e.g., the 1,4-β-D-glucan glucohydrolases; EC 3.2.1.74) liberate D-glucose from 1,4-β-D-glucans and hydrolyze D-cellobiose slowly. Cellobiohydrolases (1,4-β-D-glucan cellobiohydrolases, EC 3.2.1.91) liberate D-cellobiose from 1,4-β-glucans. β-Glucosidases ([β]-D-glucoside glucohydrolase; β-D-glucosidases; EC 3.2.1.21) act to release D-glucose units from cellobiose and soluble cellodextrins, as well as an array of glycosides. Endoglucanases act mainly on the amorphous parts of the cellulose fiber, whereas cellobiohydrolases are also able to degrade crystalline cellulose.

A combination of two or more cellulases can be used to catalyze the hydrolysis of cellulose-containing substrates. For example, endoglucanases break internal bonds and disrupt the crystalline structure of cellulose, exposing individual cellulose polysaccharide chains ("glucans"). Cellobiohydrolases incrementally shorten the glucan molecules, releasing mainly cellobiose units (a water-soluble β-1,4-linked dimer of glucose) as well as glucose, cellotriose, and cellotetrose. β-glucosidases split the cellobiose into glucose monomers. The cellulase can be a thermostable cellulase.

Cellulases suitable for use in the present invention are commercially available from, for example, Genencor (USA) and Novozymes (Europe). For instance, Novozyme has a number of different enzymes and enzyme complexes that are specifically designed to be useful for the hydrolysis of lignocellulosic materials. Examples include, but are not limited to, the following: NS50013, which is a cellulase; NS50010, which is a β-glucosidase; NS22086, which is a cellulase complex; NS22086, which is a xylanase; NS22118, which is β-glucosidase; NS22119, which is an enzyme complex of carbohydrases, including arabinase, β-glucanase, cellulase, hemicellulase, pectinase, and xylanase; NS22002, which is a mixture of β-glucanase and xylanase; and NS22035, which is a glucoamylase. In addition, suitable thermostable cellulases are disclosed in U.S. Pat. No. 9,322, 042 and PCT International Publication No. WO 2010/124266, which is incorporated herein by reference. Other hydrolases suitable for hydrolyzing the pretreated biomass, i.e., the lignocellulosic material, will be known to those of skill in the art. See, e.g., Viikari et al., *Adv. Biochem. Eng. Biotechnol.*, 108:121-45, 2007; and U.S. Pat. Nos. 8,017, 361; 8,017,373; and 8,318,461; which are incorporated herein by reference.

In some embodiments, biomass is mechanically ground, chipped, cracked, fractured, steam-exploded, ammonia fiber expanded, and/or crushed to provide lignin for use in the methods of the invention. In some such embodiment, these techniques are combined with enzymatic hydrolysis to provide the lignin-derived aromatic starting materials.

In some embodiments, the lignin-derived aromatic starting material is a technical lignin. Technical lignins are most commonly derived as a byproduct of the paper and pulp industry. For example, kraft lignin may be obtained via the kraft process; lignosulfonates, may be produced, e.g., from the sulfite pulping process; alkali lignin, may be produced, e.g., from treating the black liquor from the soda process with acid; and low sulfonate alkali lignin may be obtained as a byproduct of wood pulping. It is understood by those in the art that the precise source for technical lignin is not critical for the methods of the invention. Rather, lignin-derived aromatic starting materials from a wide range of polymeric lignin sources can be employed. In some embodiments, the technical lignin is selected from the group consisting of kraft lignin, lignosulfate, alkali lignin, and combinations thereof.

In some embodiments, the technical lignin is bagasse lignin, poplar lignin, or a combination thereof. In some embodiments of the invention, the lignin (e.g., a technical lignin) is mechanically ground, chipped, cracked, fractured, or crushed.

Lignin can also be depolymerized to provide oligomeric lignin and monomeric lignin for use as the lignin-derived aromatic starting material. Processes and agents suitable for depolymerizing lignin include those described in, e.g., by Pandey (*Chem. Eng. Technol.* 2001, 34(1): 29-41); Pearl (*J. Am. Chem. Soc.* 1942, 64 (6):1429-1431); Liu (*RSC Adv.* 2013, 3: 5789-5793); Kleen (*J. Anal. Appl. Pyrolysis.* 1991, 19: 139); and Xiang (*Appl. Biochem. Biotechnol.,* 2000, 153: 84-86), and International Pat. Appl. Publ. No. WO 2014/17204, which are incorporated herein by reference. Oxidative depolymerization methods can provide phenolic starting materials containing aldehydes, alcohols, and acids; steam explosion which provides the hemicellulose depolymerization and dehydration product furfural or 5-hydroxymethylfurfural; contacting with ionic liquids and a catalyst which provides phenols; and oxidative methods or pyrolysis with hydrogen which provide aldehydes, alcohols, and carboxylic acids.

Examples of lignin depolymerization agents for obtaining lignin-derived aromatic starting materials include, but are not limited to, ionic liquids or ionic liquid mixtures (including the ionic liquids or ionic liquid mixtures of the invention), hydrogenolysis (e.g., $H_2$ gas, a hydrogen donating agent such as tetralin, sodium formate, or formic acid), a dilute acid, a concentrated acid, a base, an oxidizing agent (e.g., nitrobenzene, a metal oxide, hydrogen peroxide, or $O_2$ gas with an appropriate catalyst), Fenton's reagent ($H_2O_2$ and ferrous sulfate), metal organic frameworks of copper or iron, and ammonium hydroxide.

As a non-limiting example, lignin or lignocellulosic biomass may be contacted with $CuSO_4$ and NaOH under conditions that yield aldehydes. Lignin or lignocellulosic biomass may also be contacted with quaternary ammonium and imidazolium dimethylphosphate ionic liquids. In addition, lignin or lignocellulosic biomass may be contacted with mild oxidants such as nitrobenzene, metal oxides, and oxygen to produce aldehydes. Similarly, depolymerization with metal organic frameworks of $Cu^{2+}$, $Fe^{3+}$, or combinations of metal ions can be used as oxidants for lignin depolymerization. Alternatively, hydrogen peroxide or Fenton's reagent may be utilized for oxidative lignin depolymerization. As yet another embodiment, oxidation may be performed under alkaline conditions.

Pyrolysis can also be employed for lignin depolymerization. In some cases, fast pyrolysis depolymerization can provide alcohols such as 4-methyl guaiacol, 4-vinyl guaiacol, trans-isoeugenol, trans-coniferyl alcohol, and aldehydes such as vanillin, and coniferaldehyde as the predominant products of lignin depolymerization. In some instances, fast pyrolysis can result in alcohols such as guaiacol, 4-vinyl guaiacol, and trans-isoeugenol as the predominant products of lignin depolymerization. In some instances, pyrolysis can provide guaiacol, syringol, and 4-vinyl syringol as the predominant products of lignin depolymerization.

In some instances, hydrogenolysis can provide phenols for use as starting materials in the methods of the invention. Hydrogenolysis can be performed, for example, at about 300-600° C. in the presence of hydrogen gas or a hydrogen donor. Suitable hydrogen donors include, but are not limited to, tetralin, sodium formate, formic acid, and the like.

Base catalyzed depolymerization can also be employed, such as described in U.S. Pat. No. 5,959,167. For example, the lignin can be contacted with a base (e.g., an alkali hydroxide) in the presence of a supercritical alcohol (e.g., methanol, ethanol, etc.). In some cases, the base catalyzed depolymerization can provide a mixture of depolymerized lignin products including alkylated phenols (e.g., mono, di, tri, and polysubstituted phenols and alkylated benzenes), alkylated benzenes, and alkoxybenzenes.

In some embodiments, the depolymerization products can be directly converted by the methods of the present invention for ionic liquid formation without extensive purification. For example, lignin may be depolymerized and converted to a lignin-derived aromatic amine or ionic liquid without purifying, or substantially purifying, the depolymerization products from other components of lignocellulosic biomass. Alternatively, lignin may be depolymerized and the depolymerization products can be purified. Methods and compositions are known in the art for purifying lignin depolymerization products.

In some embodiments, the lignin-derived aromatic starting material comprises oligomeric lignin. In some embodiments, the lignin-derived aromatic starting material is oligomeric lignin that contains primary alcohol. In some embodiments, the lignin-derived aromatic starting material is depolymerized monomeric lignin. Examples of monomeric lignin include, but are not limited to, guaiacol, syringol, 4-ethylguaiacol (i.e., 4-ethyl-2-methoxyphenol), 4-vinylguaiacol (i.e., 2-methoxy-4-vinylphenol), eugenol (i.e., 4-allyl-2-methoxyphenol), 4-(1-propenyl)guaiacol (i.e., 2-methoxy-4-(prop-1-en-1-yl)phenol), vanillin (i.e., 4-hydroxy-3-methoxybenzaldehyde), allyl syringol (i.e., 4-allyl-2,6-dimethoxyphenol), and guaiacylacetone (i.e., 1-(4-hydroxy-3-methoxyphenyl)propan-2-one). In some embodiments, the lignin-derived aromatic starting material is depolymerized lignin monomers that contain primary alcohol.

In some embodiments, the lignin-derived aromatic starting material is deoplymerized monomeric lignin comprising one or more aromatic compounds selected from the group consisting of modified phenols (i.e., substituted hydroxybenzene), modified anisoles (i.e., substituted methoxybenzene), modified guaiacols (i.e., substituted 1-hydroxy-2-methoxybenzene), modified veratroles (i.e., substituted 1,2-dimethoxybenzene), modified catechols (i.e., substituted dihydroxybenzene), and modified syringols (i.e., substituted 1-hydroxy-2,6-dimethoxybenzene).

As used herein, the terms "modified" and "substituted" as applied to lignin-derived aromatic starting material refer to an aromatic compound having from 1 to 5 substituents, each of which is independently selected from the group consisting of $C_{1-6}$ alcohol (e.g., $-CH_2OH$, $-(CH_2)_2OH$, $-(CH_2)_3OH$, $-(CH_2)_4OH$, and the like), $C_{1-6}$ alkyl (e.g., methyl, ethyl, isopropyl, and the like), $C_{2-6}$ alkenyl (e.g., vinyl, propen-1-yl, propen-2-yl, and the like), $C_{1-6}$ acyl (e.g., formyl, acetyl, and the like), and $C_{2-10}$ acylalkyl (e.g., formylmethyl, acetylmethyl, and the like). In some embodiments, the aromatic compounds are substituted with at least one $C_{1-6}$ alcohol. In some embodiments, the depolymerized lignin monomer is modified anisole. In some embodiments, the modified anisole is (4-methoxyphenyl)methanol. In some embodiments, the lignin-derived aromatic starting material comprises one or more components selected from the group consisting of sinapyl alcohol, coniferyl alcohol, and p-coumaryl alcohol.

In some embodiments, the step of contacting the lignin-derived aromatic starting material with a halogenating agent is conducted in a non-polar solvent, an aprotic solvent, or a combination thereof. In some embodiments, the non-polar solvent is selected from the group consisting of toluene, benzene, xylene, n-heptane, octane, isooctane, cyclohexane, hexane, pentane, chloroform, diethyl ether, 1,4-dioxane and combinations thereof. In some embodiments, the non-polar solvent is selected from the group consisting of diethyl ether, dioxane, chloroform, and combinations thereof. In some embodiments, the non-polar solvent is diethyl either, dioxane, and combinations thereof. In some embodiments, the lignin-derived aromatic starting material is depolymerized monomeric lignin and the halogenating step is performed in diethyl ether. In some embodiments, the lignin-derived aromatic starting material is oligomeric lignin or polymeric lignin and the halogenating step is performed in dioxane.

In some embodiments, the halogenating step is conducted in an aprotic solvent selected from dichloromethane, tetrahydrofuran, ethyl acetate, acetone, dimethylformamide, acetonitrile, dimethyl sulfoxide, propylene carbonate, and combinations thereof. In some embodiments, the aprotic solvent is dichloromethane, tetrahydrofuran, acetonitrile, and combinations thereof. In some embodiments, the halogenating step is performed in dichloromethane.

In some embodiments, the step of contacting the lignin-derived aromatic starting material with a halogenating agent is conducted at ambient temperatures of about 20° C. to 25° C. Depending on factors including, but not limited to, the particular halogenating agent employed, other reaction temperatures may be used. For example, the starting material may be contacted with the halogenating agent at a temperature ranging from −78° C. to 150° C. (e.g., from about −78° C. to about −40° C., or from about −40° C. to about 0° C., or from about 0° C. to about 4° C., or from about 4° C. to about 20° C., or from about 20° C. to about 37° C., or from about 25° C. to about 37° C., or from about 20° C. to about 40° C., or from about 20° C. to about 60° C., or from about 20° C. to about 100° C., or from about 100° C. to about 150° C.). The halogenation reaction is performed for any length of time suitable for halogenation of the lignin-derived aromatic starting material and formation of the lignin-derived aromatic halide, typically ranging from a few minutes to several hours, or longer, depending, in part, on factors such as the particular lignin-derived aromatic starting material, halogenating agent, and/or molar equivalents thereof. For example, the reaction mixture is maintained for a period of time ranging from about 6 hours to about 15 hours. In some embodiments, the reaction mixture is maintained for about 6, 7, 8, 9, 10, 11, 12, 13, 14 or 15 hours. In some embodiments, the reaction mixture is maintained for a period of time ranging from about 6 hours to about 15 hours, or from about 7 hours to about 14 hours, or from about 8 hours to about 13 hours, or from about 9 hours to about 12 hours, or from about 10 hours to about 11 hours. In some embodiments, the step of contacting the lignin-derived aromatic starting material with a halogenating agent is performed for at least about 6 hours.

The lignin-derived aromatic starting material is contacted with any amount of halogenating agent suitable for forming the lignin-derived aromatic halide. In some embodiments, the lignin-derived aromatic starting material is contacted with at least 1 molar equivalent of the halogenating agent. The lignin-derived aromatic starting material can be contacted with about 2, 3, 4, 5, 6, 7, 8, 9, or 10 molar equivalents of the halogenating agent. In some embodiments, the lignin-derived aromatic starting material is contacted with from about 1 to about 10 molar equivalents of the halogenating agent, or from about 2 to about 9 equivalents of the halogenating agent, or from about 3 to about 8 equivalents of the halogenating agent, or from about 4 to about 7 equivalents of the halogenating agent, or from about 5 to about 6 molar equivalents of the halogenating agent. In some embodiments, the lignin-derived aromatic starting material is contacted with from about 1 to about 4 molar equivalents of the halogenating agent, or from about 1 to about 3 molar equivalents of the halogenating agent, or from about 1 to about 2 molar equivalents of the halogenating agent. In some embodiments, the lignin-derived aromatic starting material is contacted with about 2 molar equivalents of the halogenating agent.

The lignin-derived aromatic starting material can be contacted with any halogenating agent suitable for forming the lignin-derived aromatic halide. In some embodiments, the halogenating agent will convert the primary alcohol moiety of the lignin-derived aromatic starting material to a halide. Examples of halogenating agents include, but are not limited to, hydrogen chloride, thionyl chloride, phosphorus trichloride, phosphorus pentachloride, hydrogen bromide, thionyl bromide, phosphorus tribromide, phosphorus pentabromide, and phosphorus triiodide. In some embodiments, the halogenating agent is hydrogen chloride, hydrogen bromide, thionyl chloride or thionyl bromide. In some embodiments, the halogenating agent is hydrogen chloride or thionyl chloride.

In some embodiments, the lignin-derived aromatic halide is a lignin-derived aromatic chloride, a lignin-derived aromatic bromide, or a lignin-derived aromatic iodide. In some embodiments, the lignin-derived aromatic halide is lignin-derived aromatic chloride or lignin-derived aromatic bromide. In some embodiments, the lignin-derived aromatic halide is lignin-derived aromatic chloride.

In some embodiments, the step of contacting the lignin-derived aromatic halide with an amine is performed in a non-polar solvent, a polar solvent, or a combination thereof. In some embodiments, the non-polar solvent is selected from the group consisting of toluene, benzene, xylene, n-heptane, octane, isooctane, cyclohexane, hexane, pentane, chloroform, diethyl ether, 1,4-dioxane and combinations thereof. In some embodiments, the non-polar solvent is selected from the group consisting of diethyl ether, dioxane, toluene, and combinations thereof. In some embodiments, the polar solvent is selected from the group consisting of n-butanol, isopropanol, n-propanol, ethanol, methanol, nitromethane, water, and combinations thereof. In some embodiments, the polar solvent is water, methanol, ethanol, or a combination thereof.

In some embodiments, the step of contacting the lignin-derived aromatic halide with an amine is performed in a combination of non-polar and polar solvents. In some embodiments, the amination step is performed in diethyl ether and water. In some embodiments, the amination step is performed in dioxane and water. In some embodiments, the lignin-derived aromatic halide is derived from depolymerized monomeric lignin and the amination step is performed in diethyl ether/water. In some embodiments, the lignin-derived aromatic halide is derived from oligomeric lignin or polymeric lignin and the amination step is performed in dioxane/water.

In some embodiments, the step of contacting the lignin-derived aromatic halide with an amine is conducted at ambient temperatures of about 20° C. to 25° C. Depending on factors including, but not limited to, the particular halide and the particular amine being employed, other reaction temperatures may be used. For example, the halide may be contacted with the amine at a temperature ranging from −78° C. to 150° C. (e.g., from about −78° C. to about −40° C., or from about −40° C. to about 0° C., or from about 0° C. to about 4° C., or from about 4° C. to about 20° C., or from about 20° C. to about 37° C., or from about 25° C. to about 37° C., or from about 20° C. to about 40° C., or from about 20° C. to about 60° C., or from about 20° C. to about 100° C., or from about 100° C. to about 150° C.). The amination reaction is performed for any length of time suitable for amination of the lignin-derived aromatic halide, forming the lignin-derived aromatic amine. Typically, the reaction mixture is maintained for a period of time ranging from about 6 hours to about 48 hours. In some embodiments, the reaction mixture is maintained for about 6, 8, 10, 12, 14, 16, 18, 20, 22, 24, 30, 36, 42, or 48 hours. In some embodiments, the reaction mixture is maintained for a period of time ranging from about 6 hours to about 48 hours, or from about 8 hours to about 42 hours, or from about 10 hours to about 36 hours, or from about 12 hours to about 30 hours, or from about 14 hours to about 24 hours, or from about 16 hours to about 22 hours, or from about 18 hours to about 20 hours. In some embodiments, the step of contacting the lignin-derived aromatic halide with an amine is performed for a period of time ranging from least about 6 hours to about 24 hours, or from least about 8 hours to about 18 hours, or from least about 10 hours to about 12 hours. In some embodiments, the step of contacting the lignin-derived aromatic halide with an amine is performed for at least 6 hours.

The lignin-derived aromatic halide is contacted with any suitable amount of amine in order to form the lignin-derived aromatic amine. In some embodiments, the lignin-derived aromatic halide is contacted with at least 1 molar equivalent of the amine. The lignin-derived aromatic halide can be contacted with about 2, 3, 4, 5, 6, 8, 10, 15, 20, 25 or 30 molar equivalents of the amine. In some embodiments, the lignin-derived aromatic halide is contacted with from about 1 to about 30 molar equivalents of the amine, or from about 2 to about 25 molar equivalents of the amine, or about from 3 to about 20 molar equivalents of the amine, or from about 4 to about 15 molar equivalents of the amine, or from about 5 to about 10 molar equivalents of the amine, or from about 6 to about 8 molar equivalents of the amine. In some embodiments, the lignin-derived aromatic halide is contacted with from about 1 to about 8 molar equivalents of the amine, or from about 1 to about 6 molar equivalents of the amine, or from about 1 to about 5 molar equivalents of the amine. In some embodiments, the lignin-derived aromatic halide is contacted with about 5 molar equivalents of the amine.

The lignin-derived aromatic halide can be contacted with any amine suitable for forming the lignin-derived aromatic amine. Conversion of the halide moiety of the lignin-derived aromatic halide with the amine can occur via a nucleophilic substitution reaction. In some embodiments, the amine is a secondary amine ($HNR_2$) or a tertiary amine ($NR_3$), wherein the R groups are independently selected from alkyl, alkenyl, alkynyl, cycloalkyl, heterocycloalkyl, aryl, or heteroaryl, among others. In some embodiments, the R groups are each an independently selected $C_{1-12}$ alkyl. R can be, for example, methyl, ethyl, n-propyl, isopropyl, n-butyl, sec-butyl, isobutyl, tert-butyl, n-pentyl, branched pentyl, n-hexyl, branched hexyl, n-heptyl, branched heptyl, n-octyl, branched octyl, n-nonyl, branched nonyl, n-decyl, branched decyl, n-undecyl, branched undecyl, n-dodecyl, or branched dodecyl. Examples of secondary amines (i.e., dialkyl amines) for use in the methods of the invention include, but are not limited to, dimethyl amine, diethyl amine, diisopropyl amine, and the like. In some embodiments, the dialkyl amine is dimethyl amine or diethyl amine. In some embodiments, the dialkyl amine is diethyl amine. Examples of tertiary amines (i.e., trialkyl amines) for use in the methods of the invention include, but are not limited to, trimethyl amine, triethyl amine, triisopropyl amine, tributyl amine, and the like. In some embodiments, the triialkyl amine is trimethyl amine, triethyl amine or tributyl amine.

In some embodiments, the step of contacting the lignin-derived aromatic amine with an acid to form the lignin-derived aromatic ammonium salt is performed in a non-polar solvent, a polar solvent, or a combination thereof. In some embodiments, the non-polar solvent is selected from the group consisting of toluene, benzene, xylene, n-heptane, octane, isooctane, cyclohexane, hexane, pentane, chloroform, diethyl ether, 1,4-dioxane and combinations thereof. In some embodiments, the non-polar solvent is selected from the group consisting of diethyl ether, dioxane, toluene, and combinations thereof. In some embodiments, the non-polar solvent is dioxane. In some embodiments, the polar solvent is selected from the group consisting of n-butanol, isopropanol, n-propanol, ethanol, methanol, nitromethane, water, and combinations thereof. In some embodiments, the polar solvent is water, methanol, ethanol, or a combination thereof. In some embodiments, the polar solvent is methanol. In some embodiments, the lignin-derived aromatic amine is derived from depolymerized monomeric lignin, and the protonation step is performed in methanol. In some embodiments, the lignin-derived aromatic amine is derived from oligomeric lignin or polymeric lignin, and the protonation step is performed in dioxane.

In some embodiments, the step of contacting the lignin-derived aromatic amine with an acid is conducted at temperatures ranging from about 0° C. to ambient temperatures of about 20° C. to 25° C. Typically, the reaction mixture will be maintained at a temperature of about 0° C. upon addition of the acid. The reaction mixture will be maintained at ambient temperatures of about 20° C. to 25° C. after addition of the acid. Depending on factors including, but not limited to, the particular acid being employed, other reaction temperatures may be used. For example, the lignin-derived aromatic amine may be contacted with the acid at a temperature ranging from −78° C. to 20° C. (e.g., from about −78° C. to about −40° C., or from about −40° C. to about 0° C., or from about −78° C. to about −4° C., or from about −40° C. to about 4° C., or from about 0° C. to about 10° C., or from about 0° C. to about 15° C.). The lignin-derived aromatic amine is contacted with an acid for any length of time suitable for protonation of the lignin-derived aromatic amine, forming the lignin-derived aromatic ammonium salt. Typically, the reaction mixture is maintained for a period of time ranging from about 6 hours to about 15 hours. In some embodiments, the reaction mixture is maintained for about 6, 7, 8, 9, 10, 11, 12, 13, 14 or 15 hours. In some embodiments, the reaction mixture is maintained for a period of time ranging from about 6 hours to about 15 hours, or from about 7 hours to about 14 hours, or from about 8 hours to about 13 hours, or from about 9 hours to about 12 hours, or from about 10 hours to about 11 hours. In some embodiments, the step of contacting the lignin-derived aromatic amine with an acid in order to form the lignin-derived aromatic ammonium salt is performed for at least about 6 hours.

The lignin-derived aromatic amine is contacted with any amount of acid suitable for forming the lignin-derived aromatic ammonium salt. The amino group of the lignin-derived aromatic amine becomes protonated to form a cation of the lignin-derived aromatic ammonium salt, which pairs with the conjugate base of the acid (i.e., the anion of the lignin-derived aromatic ammonium salt), thereby forming the ionic liquid. In some embodiments, the lignin-derived aromatic amine is contacted with at least 1 molar equivalent of the acid. The lignin-derived aromatic amine can be contacted with about 2, 3, 4, 5, 6, 8, 10, 15, 20, 25 or 30 molar equivalents of the acid. In some embodiments, the lignin-derived aromatic amine is contacted with from about 1 to about 30 molar equivalents of the acid, or from about 2 to about 25 molar equivalents of the acid, or from about 3 to about 20 molar equivalents of the acid, or from about 4 to about 15 molar equivalents of the acid, or from about 5 to about 10 molar equivalents of the acid, or from about 6 to about 8 molar equivalents of the acid. In some embodiments, the lignin-derived aromatic amine is contacted with from about 1 to about 2 molar equivalents of the acid, or from about 1 to about 3 molar equivalents of the acid, or from about 1 to about 4 molar equivalents of the acid. In some embodiments, the lignin-derived aromatic amine is contacted with about 1 molar equivalent of the acid.

The lignin-derived aromatic amine is contacted with any acid suitable for forming the lignin-derived aromatic ammonium salt. Examples of suitable acids include, but are not limited to, mineral acids (e.g., hydrochloric acid, hydrobromic acid, phosphoric acid, sulfuric acid, and the like), carboxylic acids (e.g., acetic acid, propionic acid, glutamic acid, citric acid, maleic acid, and the like), amino acids (e.g., lysine, aspartic acid, glutamic acid, and the like) and sulfonic acids (e.g., methanesulfonic acid, p-toluenesulfonic acid, and the like). In some embodiments, the acid is selected from acetic acid, sulfuric acid, phosphoric acid, and combinations thereof. In some embodiments, the acid is acetic acid. In some embodiments, the acid is sulfuric acid. In some embodiments, the acid is phosphoric acid.

Figure 1:
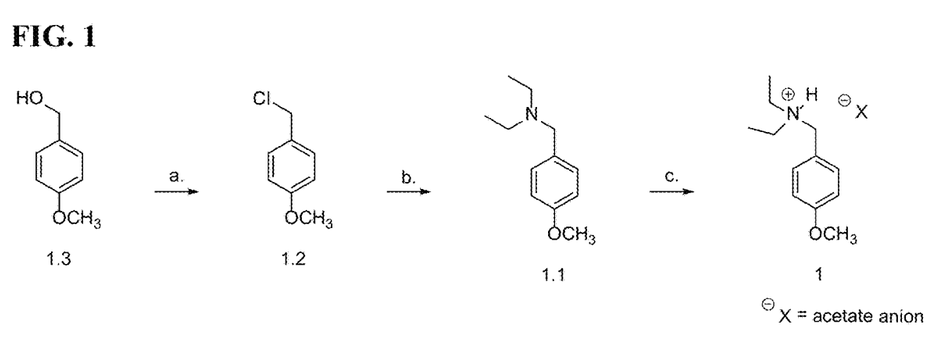
FIG. 1 shows the synthesis of anisole-based ionic liquids.
Figure 2:
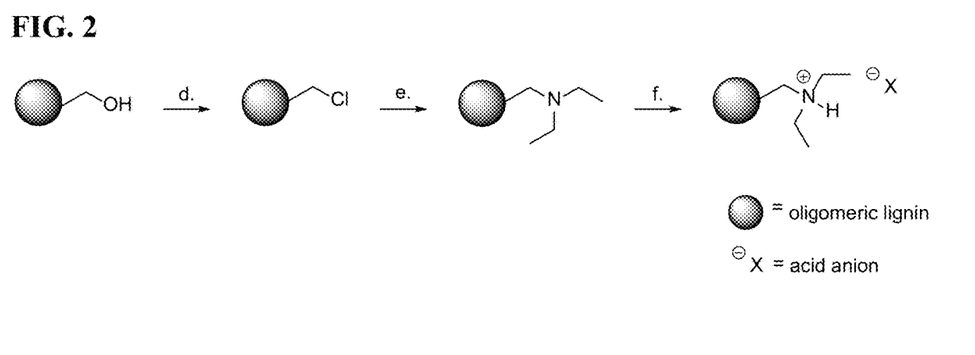
FIG. 2 shows the general synthesis of lignin-based ionic liquids using oligomeric lignin fragments.

Accordingly, the lignin-derived aromatic ammonium salts prepared according to the methods of the invention will contain one or more protonated lignin-derived aromatic ammonium cations and one or more acid anions (e.g., $X^-$ of FIG. 1 and FIG. 2) independently selected from the group consisting of acetate (as $CH_3CO_2^-$), formate (as $HCO_2^-$), lactate (as $CH_3CH(OH)CO_2^-$), citrate (e.g., as $C_3H_5O(COO)_3^{3-}$), hydrogen sulfate (as $HSO_4^-$), chloride (as $Cl^-$), nitrate (as $NO_3^-$), dihydrogen borate (as $H_2BO_3^-$), dihydrogen phosphate (as $H_2PO_4^-$), fluoride (as $F^-$), bromide (as $Br^-$), perchlorate (as $ClO_4^-$), or lysinate (as $C_{20}H_{36}N_3O_5^-$).

In some embodiments, the cation of the lignin-derived aromatic ammonium salt is a tertiary aromatic ammonium cation or a quaternary aromatic ammonium cation. In some embodiments, lignin-derived aromatic ammonium salts having a quaternary aromatic ammonium cation are generated from lignin-derived aromatic ammonium salts having a tertiary aromatic ammonium cation via an alkylation reaction. For example, quaternary lignin-derived aromatic ammonium salts may be generated via the methods and compositions described in, for example, Aresta, M. et al. *J. Mol. Catal. A: Chem.*, 2002, 182-183, 399-409; Fabris, M. et al. *Chem. Eur. J.*, 2009, 15, 12273-12282; Smiglak, M. et al. *Green Chem.*, 2010, 12, 491-501; Chiappe, C. *Green Chem.*, 2011, 13, 1437-1441; or Holbrey et al., *Green Chem.*, 2002, 4, 407-413, or a combination thereof. In some cases, dimethylsulfate or dimethyl carbonate or another methylating agent or alkylating agent (e.g., methyl halide or alkyl halide) may be utilized to generate quaternary lignin-derived aromatic ammonium salts from tertiary lignin-derived aromatic ammonium salts of the present invention. In some embodiments, the quaternary lignin-derived aromatic ammonium salt resulting from the alkylation reaction is contacted with an acid, as described above, to form an ionic liquid.

In some embodiments, the steps of contacting a lignin-derived aromatic starting material with a halogenating agent; contacting the lignin-derived aromatic halide with an amine; contacting the lignin-derived aromatic amine with an acid; and/or alkylating the tertiary lignin-derived aromatic ammonium salt are performed in a single reaction vessel. Alternatively, each intermediate lignin-derived aromatic compound (e.g., lignin-derived aromatic halide, lignin-derived aromatic amine, and/or tertiary lignin-derived aromatic ammonium salt) can be isolated from the respective reaction mixture, prior to performing any subsequent contacting step.

In some embodiments, the present invention provides an ionic liquid prepared by the foregoing methods. One of skill in the art will appreciate that lignin and lignin-derived aromatic starting materials are complex mixtures of phenylpropane polymers and oligomers that vary in structure and molecular weight distribution. Accordingly, ionic liquids prepared by the methods of the invention can be obtained as mixtures of compounds. In some embodiments, the ionic liquid contains one or more compounds having structure(s) according to Formula I, Formula II, Formula III, or Formula IV:

In come embodiments, each $R^1$ in compounds of Formula I, Formula II, Formula III, and Formula IV is independently selected from the group consisting of H and $C_{1-6}$ alkyl (e.g., —$CH_3$, —$CH_2CH_3$, or the like). In some embodiments, at least two $R^1$ groups are independently $C_{1-6}$ alkyl (e.g., —$CH_3$, —$CH_2CH_3$, or the like). In some embodiments, $R^2$, $R^3$, and $R^4$ are independently selected from the group consisting of H, hydroxy (i.e., — and $C_{1-6}$ alkoxy (e.g., —$OCH_3$ and the like). In some embodiments, $R^5$ is selected from the group consisting of H, — and hydroxy($C_{1-6}$alkyl)

(e.g., —CH$_2$OH and the like). In some embodiments, X$^-$ is an acid anion in compounds of Formula I, Formula II, Formula III, and Formula IV. In some embodiments, two R$^1$ are —CH$_2$CH$_3$; one R$^1$ is H; R$^2$, R$^3$, and R$^4$ are independently selected from the group consisting of H, —OH, and —OCH$_3$; R$^5$ is selected from the group consisting of H, —OH, and —CH$_2$OH; and X is selected from the group consisting of acetate, dihydrogen phosphate, and hydrogen sulfate.

Ionic liquids prepared according to the methods disclosed herein may contain any number of compounds, including any number of compounds according to one or more of Formula I, Formula II, Formula III, and Formula IV. The ionic liquid may be, for example, a mixture containing one or more compounds of Formula I, Formula II, Formula III, and/or Formula IV; or two or more compounds of Formula I, Formula II, Formula III, and/or Formula IV; or three or more compounds of Formula I, Formula II, Formula III, and/or Formula IV; or four or more compounds of Formula I, Formula II, Formula III, and/or Formula IV; or five or more compounds of Formula I, Formula II, Formula III, and/or Formula IV; or six or more compounds of Formula I, Formula II, Formula III, and/or Formula IV; or seven or more compounds of Formula I, Formula II, Formula III, and/or Formula IV; or eight or more compounds of Formula I, Formula II, Formula III, and/or Formula IV; or nine or more compounds of Formula I, Formula II, Formula III, and/or Formula IV; or ten or more compounds of Formula I, Formula II, Formula III, and/or Formula IV.

In some embodiments, the amount of the compound according to Formula I in the mixture (e.g., one, two, three, four, five, or more compound(s) of Formula I) is at least 50% (w/w) of the total weight of the mixture, and the total amount of compounds according to Formula II, Formula III, and/or Formula IV in the mixture is 50% (w/w) of the total weight of the mixture or less. In some embodiments, the amount of the compound according to Formula I in the mixture (e.g., one, two, three, four, five, or more compound(s) of Formula I) is at least 80% (w/w) of the total weight of the mixture, and the total amount of compounds according to Formula II, Formula III, and/or Formula IV in the mixture is 20% (w/w) of the total weight of the mixture or less. In some embodiments, the amount of the compound according to Formula I in the mixture (e.g., one, two, three, four, five, or more compound(s) of Formula I) is at least 90% (w/w) of the total weight of the mixture, and the total amount of compounds according to Formula II, Formula III, and/or Formula IV in the mixture is 10% (w/w) of the total weight of the mixture or less. In some embodiments, the amount of the compound according to Formula I in the mixture (e.g., one, two, three, four, five, or more compound(s) of Formula I) is at least 95% (w/w) of the total weight of the mixture, and the total amount of compounds according to Formula II, Formula III, and/or Formula IV in the mixture is 5% (w/w) of the total weight of the mixture or less. In some embodiments, the amount of the compound according to Formula I in the mixture (e.g., one, two, three, four, five, or more compound(s) of Formula I) is at least 99% (w/w) of the total weight of the mixture, and the total amount of compounds according to Formula II, Formula III, and/or Formula IV in the mixture is 1% (w/w) of the total weight of the mixture or less.

In some embodiments, the amount of the compound according to Formula II in the mixture (e.g., one, two, three, four, five, or more compound(s) of Formula II) is at least 50% (w/w) of the total weight of the mixture, and the total amount of compounds according to Formula I, Formula III, and/or Formula IV in the mixture is 50% (w/w) of the total weight of the mixture or less. In some embodiments, the amount of the compound according to Formula II in the mixture (e.g., one, two, three, four, five, or more compound(s) of Formula II) is at least 80% (w/w) of the total weight of the mixture, and the total amount of compounds according to Formula I, Formula III, and/or Formula IV in the mixture is 20% (w/w) of the total weight of the mixture or less. In some embodiments, the amount of the compound according to Formula II in the mixture (e.g., one, two, three, four, five, or more compound(s) of Formula II) is at least 90% (w/w) of the total weight of the mixture, and the total amount of compounds according to Formula I, Formula III, and/or Formula IV in the mixture is 10% (w/w) of the total weight of the mixture or less. In some embodiments, the amount of the compound according to Formula II in the mixture (e.g., one, two, three, four, five, or more compound(s) of Formula II) is at least 95% (w/w) of the total weight of the mixture, and the total amount of compounds according to Formula I, Formula III, and/or Formula IV in the mixture is 5% (w/w) of the total weight of the mixture or less. In some embodiments, the amount of the compound according to Formula II in the mixture (e.g., one, two, three, four, five, or more compound(s) of Formula II) is at least 99% (w/w) of the total weight of the mixture, and the total amount of compounds according to Formula I, Formula III, and/or Formula IV in the mixture is 1% (w/w) of the total weight of the mixture or less.

In some embodiments, the amount of the compound according to Formula III in the mixture (e.g., one, two, three, four, five, or more compound(s) of Formula II) is at least 50% (w/w) of the total weight of the mixture, and the total amount of compounds according to Formula I, Formula II, and/or Formula IV in the mixture is 50% (w/w) of the total weight of the mixture or less. In some embodiments, the amount of the compound according to Formula III in the mixture (e.g., one, two, three, four, five, or more compound(s) of Formula III) is at least 80% (w/w) of the total weight of the mixture, and the total amount of compounds according to Formula I, Formula II, and/or Formula IV in the mixture is 20% (w/w) of the total weight of the mixture or less. In some embodiments, the amount of the compound according to Formula III in the mixture (e.g., one, two, three, four, five, or more compound(s) of Formula III) is at least 90% (w/w) of the total weight of the mixture, and the total amount of compounds according to Formula I, Formula II, and/or Formula IV in the mixture is 10% (w/w) of the total weight of the mixture or less. In some embodiments, the amount of the compound according to Formula III in the mixture (e.g., one, two, three, four, five, or more compound(s) of Formula III) is at least 95% (w/w) of the total weight of the mixture, and the total amount of compounds according to Formula I, Formula II, and/or Formula IV in the mixture is 5% (w/w) of the total weight of the mixture or less. In some embodiments, the amount of the compound according to Formula III in the mixture (e.g., one, two, three, four, five, or more compound(s) of Formula III) is at least 99% (w/w) of the total weight of the mixture, and the total amount of compounds according to Formula I, Formula II, and/or Formula IV in the mixture is 1% (w/w) of the total weight of the mixture or less.

In some embodiments, the amount of the compound according to Formula IV in the mixture (e.g., one, two, three, four, five, or more compound(s) of Formula IV) is at least 50% (w/w) of the total weight of the mixture, and the total amount of compounds according to Formula I, Formula II, and/or Formula III in the mixture is 50% (w/w) of the total weight of the mixture or less. In some embodiments, the amount of the compound according to Formula IV in the mixture (e.g., one, two, three, four, five, or more compound(s) of Formula IV) is at least 80% (w/w) of the total weight of the mixture, and the total amount of compounds according to Formula I, Formula II, and/or Formula III in the mixture is 20% (w/w) of the total weight of the mixture or less. In some embodiments, the amount of the compound according to Formula IV in the mixture (e.g., one, two, three, four, five, or more compound(s) of Formula IV) is at least 90% (w/w) of the total weight of the mixture, and the total amount of compounds according to Formula I, Formula II, and/or Formula III in the mixture is 10% (w/w) of the total weight of the mixture or less. In some embodiments, the amount of the compound according to Formula IV in the mixture (e.g., one, two, three, four, five, or more compound(s) of Formula IV) is at least 95% (w/w) of the total weight of the mixture, and the total amount of compounds according to Formula I, Formula II, and/or Formula III in the mixture is 5% (w/w) of the total weight of the mixture or less. In some embodiments, the amount of the compound according to Formula IV in the mixture (e.g., one, two, three, four, five, or more compound(s) of Formula IV) is at least 99% (w/w) of the total weight of the mixture, and the total amount of compounds according to Formula I, Formula II, and/or Formula III in the mixture is 1% (w/w) of the total weight of the mixture or less.

IV. Examples

The following examples are provided by way of illustration only and not by way of limitation. Those of skill will readily recognize a variety of noncritical parameters which could be changed or modified to yield essentially similar results.

Example 1. Synthesis of 1-(chloromethyl)-4-methoxybenzeneloride (1.2) via Halogenation (Step 1)

In a 250 mL round bottom flask, (4-methoxyphenyl)methanol (1.3, 5.0 g, 36 mmol), which can be obtained via depolymerization of lignin as described above, was dissolved in 100 mL diethyl ether (Et$_2$O). At room temperature thionyl chloride (SOCl$_2$, 8.6 g, 72 mmol) was dropwise added to the reaction mixture. Upon addition the reaction mixture was allowed to stir at room temperature for 6 hrs. Then the reaction was quenched by slow addition of 100 mL cold water. The reaction mixture was extracted with methylene chloride (3×50 mL). The organic layers were combined and dried over magnesium sulfate (MgSO$_4$), and solvent was removed to provide 1-(chloromethyl)-4-methoxybenzeneloride (1.2, 5.1 g, 90% yield) as a colorless oil.

Example 2. Synthesis of N-ethyl-N-(4-methoxybenzyl)ethanamine (1.1) via Amination (Step 2)

To a solution of 1-(chloromethyl)-4-methoxybenzeneloride (1.2, 3.0 g, 19 mmol) in 50 mL diethyl ether was added a solution of 50 wt. % aqueous diethyl amine solution (DEA, 7.0 g, 95 mmol) at room temperature. After stirring overnight at room temperature, the solution was quenched by adding aqueous 3 M HCl (pH~1). The aqueous phase was washed with dichloromethane. The pH of the aqueous phase was raised to ~9.5 by addition of 3 M KOH, and the product was extracted two times with ethyl acetate. The combined organic layers were dried over MgSO$_4$ and concentrated to provide N-ethyl-N-(4-methoxybenzyl)ethanamine as a light yellow liquid (1.1, 3.4 g, 92% yield).

Example 3. Synthesis of N-ethyl-N-(4-methoxybenzyl)ethanaminium Acetate (1) Via Protonation (Step 3)

To a stirred solution of N-ethyl-N-(4-methoxybenzyl)ethanamine (1.1, 2.0 g, 10.3 mmol) in 25 mL methanol (MeOH) at 0° C. was slowly added acetic acid (C$_2$H$_4$O$_2$, 0.62 g, 10.3 mmol). The solution was allowed to stir, warming to room temperature for 6 h. Methanol was evaporated under vacuum and the ionic liquid N-ethyl-N-(4-methoxybenzyl)ethanaminium acetate (1) was obtained as a light brown liquid (2.5 g, 95% yield).

V. Exemplary Embodiments

Aspects of the present disclosure include, but are not limited to, the appended claims and the following exemplary embodiments:

1. A process for preparing an ionic liquid comprising:
   contacting a lignin-derived aromatic starting material with a halogenating agent under conditions sufficient to form a lignin-derived aromatic halide;
   contacting the lignin-derived aromatic halide with an amine under conditions sufficient to form a lignin-derived aromatic amine; and
   contacting the lignin-derived aromatic amine with an acid under conditions sufficient to form a lignin-derived aromatic ammonium salt, thereby preparing the ionic liquid.

2. The method of embodiment 1, wherein the lignin-derived aromatic starting material comprises a primary alcohol.

3. The method of embodiment 1 or embodiment 2, wherein the lignin-derived aromatic starting material comprises one or more components selected from the group consisting of depolymerized lignin monomers, oligomeric lignin, polymeric lignin, and lignocellulose.

4. The method of embodiment 3, further comprising depolymerizing lignin to obtain the depolymerized lignin monomers, the oligomeric lignin, or a combination thereof.

5. The method of embodiment 3 or embodiment 4, wherein the depolymerized lignin monomers comprise one or more components selected from the group consisting of modified phenols, modified anisoles, modified guaiacols, modified veratroles, modified catechols, and modified syringols.

6. The method of embodiment 5, wherein the modified anisole is (4-methoxyphenyl)methanol.

7. The method of embodiment 1, wherein the lignin-derived aromatic starting material comprises one or more components selected from the group consisting of sinapyl alcohol, coniferyl alcohol, and p-coumaryl alcohol.

8. The method of any one of the preceding embodiments, wherein the lignin-derived aromatic starting material is contacted with the halogenating agent in the presence of a non-polar solvent, an aprotic solvent, or a combination thereof.

9. The method of embodiment 8, wherein the non-polar solvent is selected from the group consisting of diethyl ether, dioxane, and chloroform.

10. The method of embodiment 8, wherein the aprotic solvent is selected from the group consisting of dichloromethane, tetrahydrofuran, and acetonitrile.

11. The method of any one of the preceding embodiments, wherein the lignin-derived aromatic starting material is contacted with the halogenating agent at a temperature ranging from about 20° C. to about 25° C.

12. The method of any one of the preceding embodiments, wherein the lignin-derived aromatic starting material is contacted with the halogenating agent for at least 6 hours.

13. The method of any one of the preceding embodiments, wherein the lignin-derived aromatic starting material is contacted with from about 1 to about 3 molar equivalents of the halogenating agent.

14. The method of any one of the preceding embodiments, wherein the halogenating agent is selected from the group consisting of hydrogen chloride, thionyl chloride, phosphorus trichloride, phosphorus pentachloride, hydrogen bromide, thionyl bromide, phosphorus tribromide, phosphorus pentabromide, and phosphorus triiodide.

15. The method of any one of the preceding embodiments, wherein the lignin-derived aromatic halide is a chloride, a bromide, or an iodide.

16. The method of any one of the preceding embodiments, wherein the halogenating agent is hydrogen chloride or thionyl chloride.

17. The method of any one of the preceding embodiments, wherein the lignin-derived aromatic halide is a chloride.

18. The method of any one of the preceding embodiments, wherein the lignin-derived aromatic halide is contacted with the amine in the presence of a non-polar solvent, a polar solvent, or a combination thereof.

19. The method of embodiment 18, wherein the non-polar solvent is selected from the group consisting of diethyl ether, dioxane, and toluene.

20. The method of embodiment 18, wherein the polar solvent is selected from the group consisting of water, methanol, and ethanol.

21. The method of any one of embodiments 18 to 20, wherein the combination comprises diethyl ether and water or dioxane and water.

22. The method of any one of the preceding embodiments, wherein the lignin-derived aromatic halide is contacted with the amine at a temperature ranging from about 20° C. to about 25° C.

23. The method of any one of the preceding embodiments, wherein the lignin-derived aromatic halide is contacted with the amine for at least 6 hours.

24. The method of any one of the preceding embodiments, wherein the lignin-derived aromatic halide is contacted with from about 1 to about 6 molar equivalents of the amine.

25. The method of any one of the preceding embodiments, wherein the amine is a secondary amine or a tertiary amine.

26. The method of embodiment 25, wherein the secondary amine is a dialkyl amine.

27. The method of embodiment 26, wherein the dialkyl amine is dimethyl amine or diethyl amine.

28. The method of embodiment 25, wherein the tertiary amine is a trialkyl amine.

29. The method of embodiment 28, wherein the trialkyl amine is trimethyl amine, triethyl amine, or tributyl amine.

30. The method of any one of the preceding embodiments, wherein the lignin-derived aromatic amine is contacted with the acid in the presence of a non-polar solvent, a polar solvent, or a combination thereof. 31. The method of embodiment 30, wherein the non-polar solvent is selected from the group consisting of diethyl ether, dioxane, and toluene.

32. The method of embodiment 30 or embodiment 31, wherein the non-polar solvent is dioxane.

33. The method of embodiment 30, wherein the polar solvent is selected from the group consisting of water, methanol, and ethanol.

34. The method of embodiment 30 or embodiment 33, wherein the polar solvent is methanol.

35. The method of any one of the preceding embodiments, wherein the lignin-derived aromatic amine is contacted with the acid at a temperature ranging from about 0° C. to about 25° C.

36. The method of any one of the preceding embodiments, wherein the lignin-derived aromatic amine is contacted with the acid for at least 6 hours.

37. The method of any one of the preceding embodiments, wherein the lignin-derived aromatic amine is contacted with from about 1 to about 2 molar equivalents of the acid.

38. The method of any one of the preceding embodiments, wherein the acid is selected from the group consisting of acetic acid, sulfuric acid, and phosphoric acid.

39. The method of embodiment 38, wherein the acid is acetic acid.

40. The method of any one of the preceding embodiments, wherein the contacting steps are performed in a single reaction vessel.

41. An ionic liquid prepared by the method of any one of the preceding embodiments.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for preparing an ionic liquid comprising:
   (i) contacting a lignin-derived aromatic starting material with a halogenating agent in a non-polar solvent, an aprotic solvent, or a combination thereof under conditions sufficient to form a lignin-derived aromatic halide;
   (ii) contacting the lignin-derived aromatic halide with an amine under conditions sufficient to form a lignin-derived aromatic amine; and
   (iii) contacting the lignin-derived aromatic amine with an acid under conditions sufficient to form a lignin-derived aromatic ammonium salt, thereby preparing the ionic liquid.

2. The method of claim 1, wherein the lignin-derived aromatic starting material comprises a primary alcohol.

3. The method of claim 1, wherein the lignin-derived aromatic starting material comprises one or more components selected from the group consisting of depolymerized lignin monomers, oligomeric lignin, polymeric lignin, and lignocellulose.

4. The method of claim 3, further comprising depolymerizing lignin to obtain the depolymerized lignin monomers, the oligomeric lignin, or a combination thereof.

5. The method of claim 3, wherein the depolymerized lignin monomers comprise one or more components selected from the group consisting of modified phenols, modified anisoles, modified guaiacols, modified veratroles, modified catechols, and modified syringols.

6. The method of claim 5, wherein the modified anisole is (4-methoxyphenyl)methanol.

7. The method of claim 1, wherein the lignin-derived aromatic starting material comprises one or more components selected from the group consisting of sinapyl alcohol, coniferyl alcohol, and p-coumaryl alcohol.

8. The method of claim 1, wherein the halogenating agent is selected from the group consisting of hydrogen chloride, thionyl chloride, phosphorus trichloride, phosphorus pentachloride, hydrogen bromide, thionyl bromide, phosphorus tribromide, phosphorus pentabromide, and phosphorus triiodide.

9. The method of claim 1, wherein the lignin-derived aromatic halide is contacted with from about 1 to about 6 molar equivalents of the amine.

10. The method of claim 1, wherein the amine is a secondary amine or a tertiary amine.

11. The method of claim 10, wherein the secondary amine is a dialkyl amine.

12. The method of claim 10, wherein the tertiary amine is a trialkyl amine.

13. The method of claim 1, wherein step (i) and step (ii) is conducted at a temperature independently ranging from about 0° C. to about 25° C.

14. The method of claim 1, wherein step (iii) is conducted at a temperature ranging from about 0° C. to about 25° C.

15. The method of claim 1, wherein at least one of step (i), step (ii), and step (iii) is conducted for at least 6 hours.

16. The method of claim 1, wherein the lignin-derived aromatic amine is contacted with from about 1 to about 2 molar equivalents of the acid.

17. The method of claim 1, wherein the acid is selected from the group consisting of acetic acid, sulfuric acid, and phosphoric acid.

18. The method of claim 1, wherein the contacting steps are performed in a single reaction vessel.

19. An ionic liquid prepared by the method of claim 1.

20. The method of claim 1, wherein the non-polar solvent is selected from the group consisting of diethyl ether, dioxane, and chloroform, and wherein the aprotic solvent is selected from the group consisting of dichloromethane, tetrahydrofuran, and acetonitrile.

* * * * *